(12) United States Patent
Levinson et al.

(10) Patent No.: US 11,197,654 B2
(45) Date of Patent: Dec. 14, 2021

(54) DYNAMIC BOWTIE FILTER AND METHODS OF USING THE SAME

(71) Applicant: KONINKLIJKE PHILIPS N.V., Eindhoven (NL)

(72) Inventors: Reuven Levinson, Haifa (IL); Mark Kenneth Limkeman, Highland Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/644,646

(22) PCT Filed: Sep. 5, 2018

(86) PCT No.: PCT/EP2018/073908
§ 371 (c)(1),
(2) Date: Mar. 5, 2020

(87) PCT Pub. No.: WO2019/048502
PCT Pub. Date: Mar. 14, 2019

(65) Prior Publication Data
US 2021/0059633 A1 Mar. 4, 2021

Related U.S. Application Data

(60) Provisional application No. 62/555,815, filed on Sep. 8, 2017.

(51) Int. Cl.
*A61B 6/00* (2006.01)
*A61B 6/03* (2006.01)

(52) U.S. Cl.
CPC .............. *A61B 6/542* (2013.01); *A61B 6/032* (2013.01); *A61B 6/4035* (2013.01); *A61B 6/488* (2013.01)

(58) Field of Classification Search
CPC ....... A61B 6/542; A61B 6/032; A61B 6/4035; A61B 6/488; G21K 1/046; G21K 1/10
See application file for complete search history.

(56) References Cited

U.S. PATENT DOCUMENTS

2005/0089135 A1* 4/2005 Toth ........................ A61B 6/032
378/16
2005/0089136 A1* 4/2005 Toth ...................... A61B 6/4035
378/16
(Continued)

FOREIGN PATENT DOCUMENTS

EP 1498908 A2 1/2005
WO WO2012104751 A1 8/2012
(Continued)

OTHER PUBLICATIONS

PCT International Search Report, International application No. PCT/EP2018/073908, dated Feb. 8, 2018.
(Continued)

*Primary Examiner* — Courtney D Thomas
(74) *Attorney, Agent, or Firm* — Larry Liberchuk

(57) ABSTRACT

An imaging system (100) includes a radiation source (708) that emits radiation that traverses an examination region (706), a radiation detector array (716) with a plurality of detectors (1104N) that detect the radiation that traverses the examination region, a dynamic bowtie filter (718) between the radiation source and the examination region, a first motor (7221) and a second motor (7222), and a controller (724). The dynamic bowtie filter includes a first half wedge (7181) and a second half wedge (7182). The first motor is in mechanical communication with the first half wedge and moves the first half wedge and the second motor is in mechanical communication with the second half wedge and moves the second half wedge. The controller independently controls the first and second motors to move the first and second half wedges.

13 Claims, 8 Drawing Sheets

(56) References Cited

U.S. PATENT DOCUMENTS

| | | | |
|---|---|---|---|
| 2005/0089146 A1* | 4/2005 | Toth | G21K 1/04 |
| | | | 378/158 |
| 2006/0018435 A1 | 1/2006 | Toth | |
| 2006/0072705 A1 | 4/2006 | Munro | |
| 2007/0025520 A1 | 2/2007 | Thandiackal | |

FOREIGN PATENT DOCUMENTS

| | | |
|---|---|---|
| WO | WO2012174246 A2 | 12/2012 |
| WO | WO2015022599 A1 | 2/2015 |

OTHER PUBLICATIONS

Kim M.S. et al., "Relationship Between Patient Centering, Mean Computed Tomography Numbers and Noise in Abdominal Computed Tomography: Influence of Anthropomorphic Parameters", World Journal of Radiology, vol. 4, Issue pp. 102-108, Mar. 28, 2012.

Habibzadeh M.A. et al., "Impact of Miscentering on Patient Dose and Image Noise in X-Ray CT Imaging: Phantom and Clinical Studies", Physica Medica, European Journal of Medical Physics, vol. 28, issue 3, pp. 191-199, Jul. 2012.

Toth T. et al., "The Influence of Patient Centering on CT Dose and Image Noise", Medical Physics, vol. 34, Issue 7, pp. 3093-3101, Jul. 2007.

* cited by examiner

DYNAMIC BOWTIE FILTER AND METHODS OF USING THE SAME

FIELD OF THE INVENTION

The following generally relates to imaging and more particular to a dynamic bowtie filter utilized to reduce radiation delivered to off-centered objects in a CT-scanner.

BACKGROUND OF THE INVENTION

A computed tomography (CT) scanner includes an X-ray tube that emits radiation and that is mounted on a rotatable gantry that rotates around an examination region about a z-axis. A source collimator is disposed between the x-ray tube and the examination region and collimates the radiation to produce an X-ray radiation beam. The beam traverses the examination region and an object or subject therein (which attenuates the beam as a function of the radiodensity of the object or subject) and illuminates a detector array disposed across the examination region from the X-ray tube. The detector produces projection data indicative of the detected radiation, and the projection data is reconstructed to generate volumetric image data indicative of the subject or object. A filter, referred to as a "bowtie" filter, due to its shape, is located between the x-ray tube and the source collimator and spatially attenuates the beam. Due to its shape (e.g., thinner at a central region and thicker at the periphery regions), the bowtie filter heavily attenuates regions of the beam at the periphery of the beam, lightly attenuates the region about the center of the beam, and varies the degree of attenuation there between. As a result of the beam attenuation, the X-ray radiation dose to the object or subject is reduced.

A currently available commercial CT system has a bowtie filter mounted on the rotatable gantry. The bowtie filter is fixed (static), relative to the X-ray tube, and is designed to reduce the x-ray fluence modulation at the detector array, relative to a configuration with no bowtie filter, when scanning a subject. Optimal dose reduction occurs when the geometric center of the object or subject coincides with the iso-center of the CT scanner. For a centered object or subject, the range of fluence to the detector array and the absorbed dose in the patient are minimized. For a mis-centered subject or object, the range of the fluence to the detector array and the patient dose are increased. In general, mis-centering means the geometric center of the object or subject does not coincide with (or is off-center with respect to) the iso-center of the CT scanner. As a result of mis-centering, the static bowtie filter may not produce an optimized fluence modulation at the detector array, and thus dose reduction is not optimized. The literature indicates that because of mis-centering, the increase in dose (versus a centered subject) may be thirty-three percent (33%).

An example of mis-centering of an object with respect to an iso-center of a CT scanner with a static bowtie filter is shown in FIGS. 1-6. FIGS. 1 and 2 show a CT scanner 100 with a single X-ray tube 104 and a static bowtie filter 102 rotating through several different angular positions $101_1$, $101_2$, $101_3$, $101_4$, and $101_5$. In FIGS. 1 and 3, an object 106 is centered at an iso-center 108 of the CT scanner 100. That is, a geometric center 110 of the object 106 coincides with the iso-center 108 of the CT system 100. In FIG. 2, the object 106 is off-center or not centered in the CT scanner 100, and the geometric center 110 of the object 106 is above the iso-center 108 of the CT scanner. As a result, the object 106 may be subject to a dose greater at a region 112, which includes a bottom and an outer perimeter, relative to if the geometric center 110 were centered at the iso-center 108. FIG. 4 shows an example where the geometric center 110 of the object 106 is below the iso-center 108, FIG. 5 shows an example where the geometric center 110 is to the right of the iso-center 108, and FIG. 6 shows an example where the geometric center 110 is to the left of the iso-center 108. Each of these situations may also result in increased dose relative to FIGS. 1 and 3.

SUMMARY OF THE INVENTION

Aspects described herein address the above-referenced problems and/or others.

In one aspect, an imaging system includes a radiation source that emits radiation that traverses an examination region, a radiation detector array with a plurality of detectors that detect the radiation that traverses the examination region, a dynamic bowtie filter between the radiation source and the examination region, a first and second motor, and a controller. The dynamic bowtie filter includes a first and second half wedge with a material free space there between. The first motor is in mechanical communication with the first half wedge and moves the first half wedge, and the second motor is in mechanical communication with the second half wedge and moves the second half wedge. The controller independently controls the first and second motors to move the first and second half wedges to increase or decrease the distance there between during an acquisition interval.

In another aspect, a computer readable storage medium is encoded with computer executable instructions, which when executed by a processor, causes the processor to obtain one of more projection image(s) of a subject or object generated with one of more survey scan(s) of the subject or object, creates a mathematical ellipse for the subject or object from the projection image(s) and calculates, for an acquisition angle, a first fluence at a detector of a detector array with the mathematical ellipse with a first half wedge or a second half wedge of a bowtie filter at a first position. The instructions, when executed by the processor, further causes the processor to compare the first calculated fluence with a predetermined fluence acceptance criterion and add the first position to a position profile only in response to the first calculated fluence satisfying the predetermined fluence acceptance criterion.

In another aspect, a method includes attenuating rays of an emitted radiation beam during a scan of a subject or object with a dynamic bowtie filter. The dynamic bowtie filter includes a first half wedge and a second half wedge. The method further includes independently moving, with a controller, the first half wedge and the second half wedge to increase or decrease a distance between the first and second half wedges during a scan based on a predetermined wedge position profile.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 2:
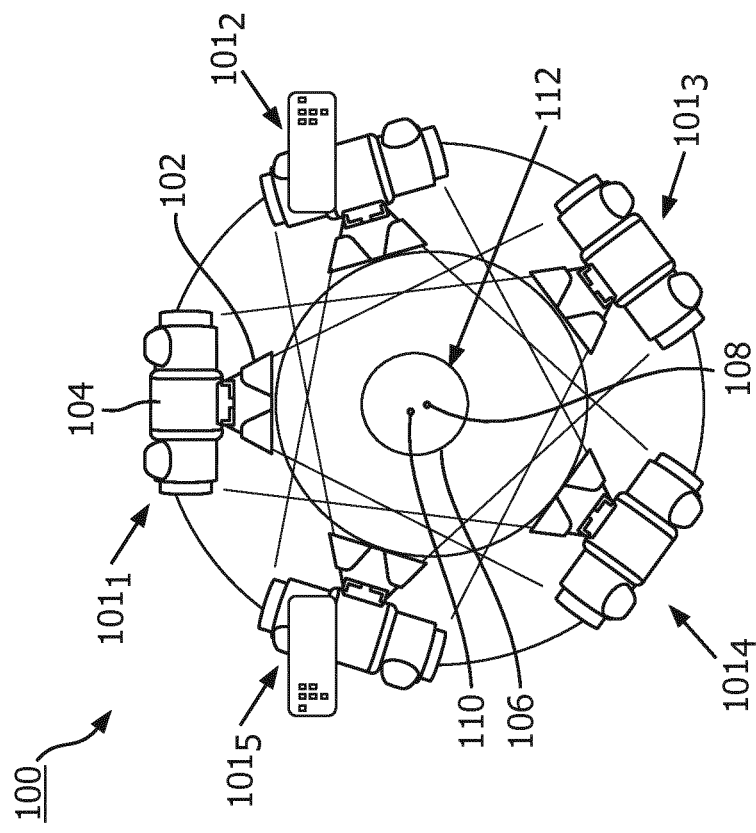
FIG. 2 illustrates the CT scanner with the prior art static bowtie filter where the center of the object is above (off-center, or not center with) the iso-center.
Figure 1:
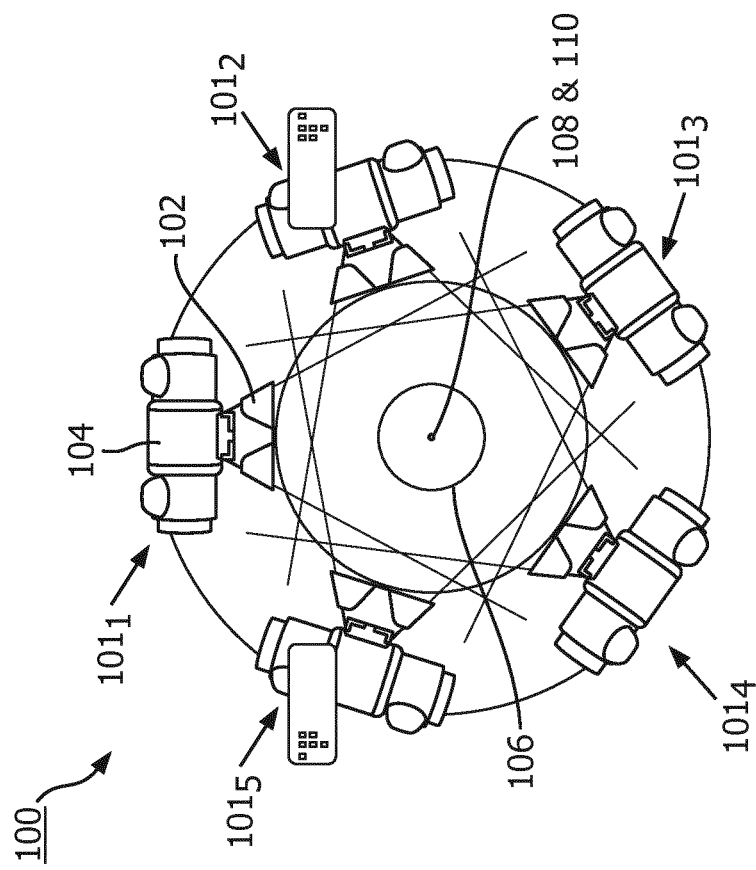
FIG. 1 illustrates a CT scanner with a prior art static bowtie filter where a center of an object is centered at an iso-center.
Figure 3:
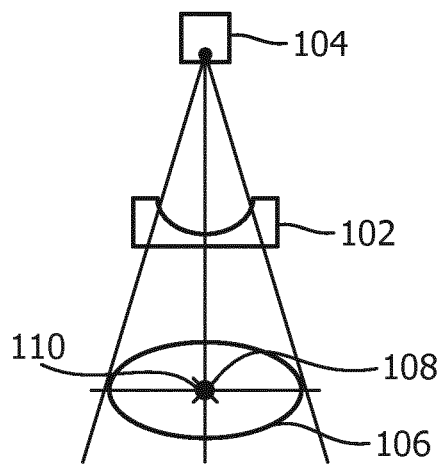
FIG. 3 illustrates the CT scanner with the prior art static bowtie filter where the center of the object is centered at the iso-center.
Figure 4:
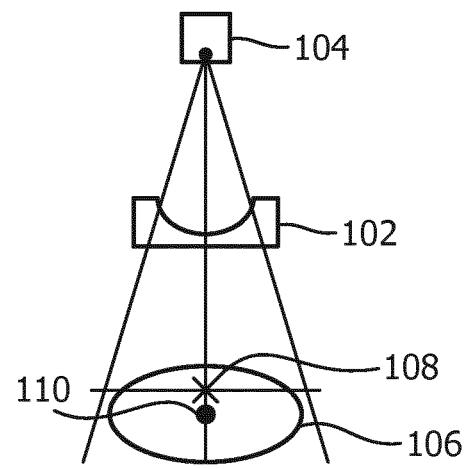
FIG. 4 illustrates the CT scanner with the prior art static bowtie filter where the center of the object is below the iso-center.
Figure 5:
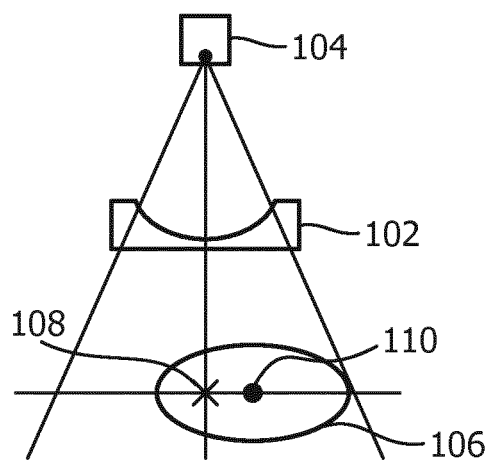
FIG. 5 illustrates the CT scanner with the prior art static bowtie filter where the center of the object is to the right of the iso-center.
Figure 6:
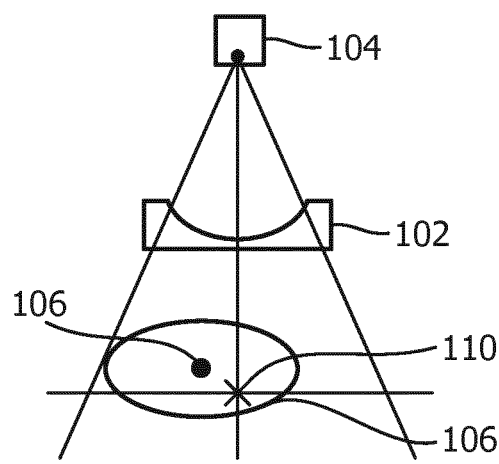
FIG. 6 illustrates the CT scanner with the prior art static bowtie filter where the center of the object is to the left of the iso-center.
Figure 7:
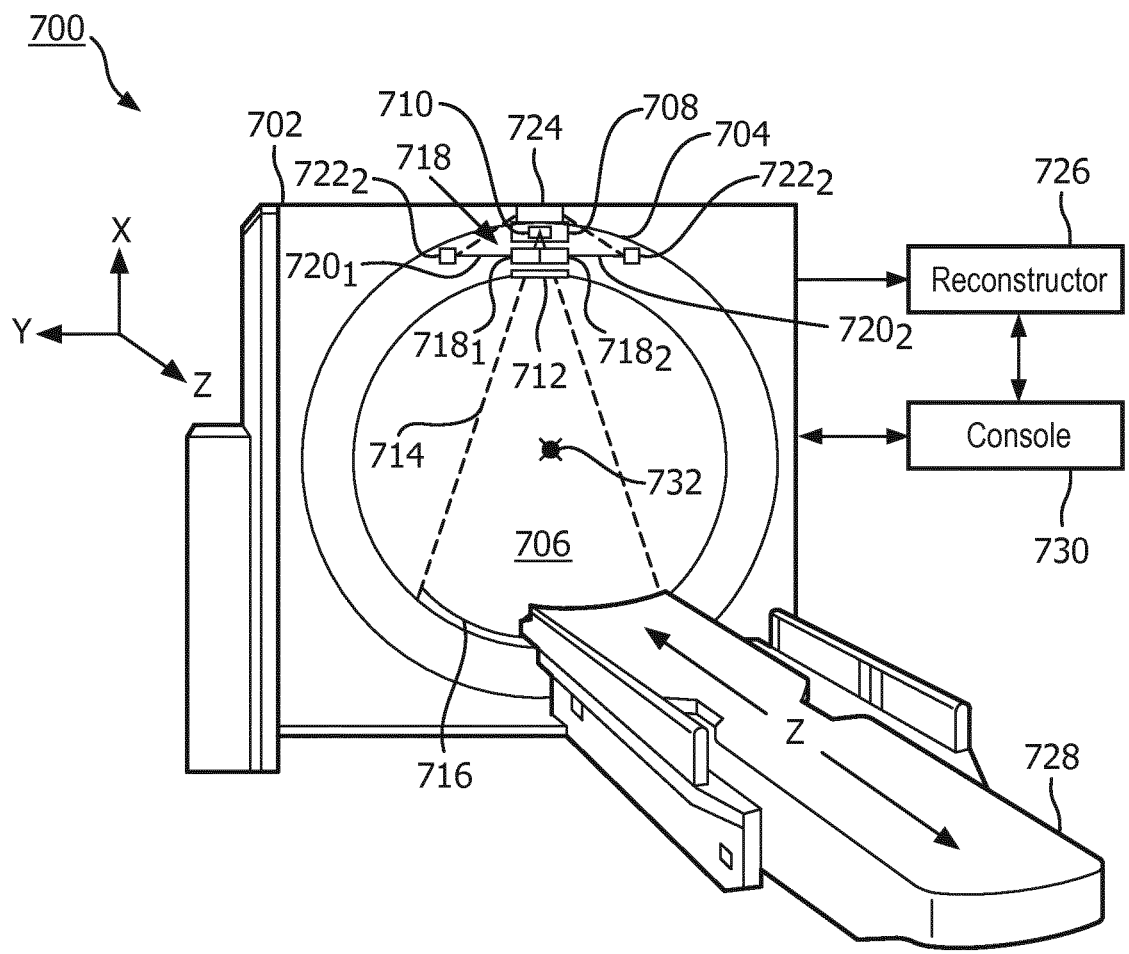
FIG. 7 diagrammatically illustrates an example imaging system with a dynamic bowtie filter in accordance with an embodiment described herein.

FIG. 7 diagrammatically illustrates an imaging system 700 such as a computed tomography (CT) scanner. The imaging system 700 includes a generally stationary gantry 702 and a rotating gantry 704, which is supported by the stationary gantry 702 via a bearing (not visible) or the like. The rotating gantry 704 rotates around an examination region 706 about a longitudinal or z-axis ("Z"). A radiation source 708, such as an X-ray tube, is supported by and rotates with the rotating gantry 704 and emits X-ray radiation via a focal spot 710 of the radiation source 708.

A source collimator 712 is disposed between the radiation source 708 and the examination region 706 and collimates the emitted radiation to produce a collimated beam 714 having a pre-determined geometrical shape (e.g., fan, wedge, cone, etc.). The collimated beam 714 traverses the examination region 706 (and a portion of any object or subject therein, which attenuates the beam as a function of the radiodensity of the object or subject) and illuminates a radiation sensitive detector array 716. The radiation sensitive detector array 716 subtends an angular arc opposite the radiation source 708 across the examination region 706 and includes a plurality of detectors that detect radiation traversing the examination region 706 and outputs an electrical signal (line integrals, intensity data, or projection data) indicative thereof.

A dynamic bowtie filter 718 is arranged between the x-ray tube 708 and the collimator 712 and attenuates the collimated beam. In the illustrated example, the dynamic bowtie filter 718 comprises two half wedges $718_1$ and $718_2$ that spatially attenuate the emitted radiation to shape the X-ray fluence profile. Each half wedge $718_1$ and $718_2$ is coupled to a half wedge holder (not visible), which are coupled to movers $720_1$ and $720_2$, which are coupled to motors $722_1$ and $722_2$. In one embodiment, the movers $720_1$ and $720_2$ are linear stages and the motors $722_1$ and $722_2$ are linear motors. An example of a suitable linear stage includes products of Chieftek Precision Co. (CPC), LTD, Tainan, Taiwan. In other embodiments, the movers $720_1$ and $720_2$ may include at least a lead screw, a ball screw, a chain, a gear, or the like, driven with a suitable motor. The movers $720_1$ and $720_2$ can be coupled to the half wedge holders and/or the motors $722_1$ and $722_2$ via a fastener such as an adhesive (e.g., glue), a screw, a rivet, a clamp, and the like.

A controller 724 controls one or both of the motors $722_1$ and $722_2$ to move the movers $720_1$ and $720_2$ and hence the half wedges $718_1$ and $718_2$. In one instance, such control includes complete independent control of the two half-wedges in which movement of one of the half wedges $718_1$ and $718_2$ is independent of movement of the other of the half wedges $718_1$ and $718_2$. With this control, the half wedges $718_1$ and $718_2$ can both be moved in a same direction or in different directions at any point in time. This also includes moving only one of the half wedges $718_1$ and $718_2$. Optional control includes moving the half wedges $718_1$ and $718_2$ such that movement of one of the half wedges $718_1$ and $718_2$ is dependent on movement of the other of the half wedges $718_1$ and $718_2$. This may include moving them in a same direction, by an approximately same distance, with an approximately same velocity, at an approximately same time, all within pre-determined tolerances.

As described in greater detail below, the dynamic bowtie filter 718 is configured to dynamically move one or both (individually and/or concurrently) of the wedges $718_1$ and $718_2$ to adjust the X-ray fluence profile, e.g., through a physical movement (e.g., translation) of one or more of the wedges $718_1$ and $718_2$ relative to source 708. In one instance, the movement compensates for an object or subject positioned off-center with respect to iso-center 732 of the imaging system 700, where a center of geometry of the object is above, below, to the left of, or to the right, or a combination thereof, of the iso-center 732. As such, the system(s) and/or method(s) described herein, in one instance, can mitigate overdose resulting from mis-centering (described herein in connection with FIGS. 1-6) an object or subject in the examination region 706 of the imaging system 700.

A reconstructor 726 reconstructs the electrical signals and generates three-dimensional volumetric image data. Example processing when using a filtered back-projection reconstruction algorithm includes, for each view, normalize the intensity data output by the detector array 716, perform a mathematical logarithm operation on the normalized intensity data, remove attenuation of the dynamic bowtie filter 718 from the logged data, optionally perform a correction (e.g., a beam hardening correction), back-project the corrected data, and convolve the back-projected data with a high pass filter. The volumetric image data (tomographic images) is generated therefrom. Generally, a view is the data collected across the detector array for an acquisition angle, and an acquisition interval refers to a period of time wherein the collimated beam illuminates the detector array and the detector array 716 detects the radiation over a predetermined angular increment of the rotating gantry. This is referred to as an integration period.

A subject support 728, such as a couch, supports a subject or an object in the examination region 706. A general purpose computing system serves as an operator console 730, which includes human readable output devices such as a display and/or printer and input devices such as a keyboard and/or mouse and allows the operator to control the operation of the system 700, for example, allowing the operator to select a protocol that employs the dynamic bowtie filter 718, initiate scanning, etc. The console 730 includes one or more computer processors (e.g., a central processing unit or CPU, a microprocessor, etc.) and computer readable storage medium, which excludes transitory medium, such as physical memory, a memory device, and/or other non-transitory storage medium. The computer readable storage medium includes one or more computer readable instructions. The one or more computer processors are configured to execute at least one of the one or more computer readable instructions and/or instructions carried by a carrier wave, a signal and/or other transitory medium.

In a variation, the imaging system 700 includes multiple radiation sources 708 and multiple dynamic bowtie filters 718.

Figure 8:
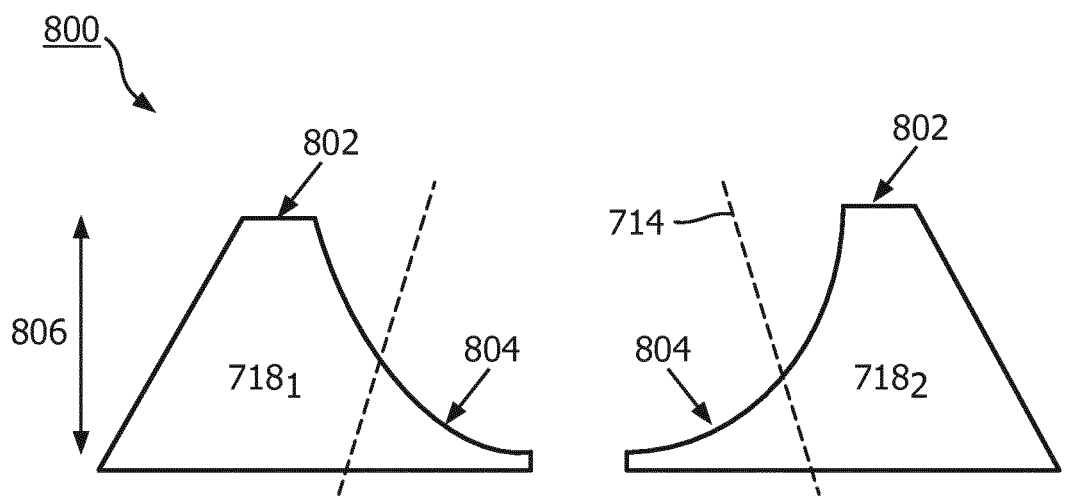
FIG. 8 diagrammatically illustrates an example of the dynamic bowtie filter in accordance with an embodiment herein.

FIG. 8 diagrammatically illustrates an example embodiment 800 of the dynamic bowtie filter 718 comprising separate and distinct (not connected) half wedges 718$_1$ and 718$_2$. The half wedges 718$_1$ and 718$_2$ have a greater thickness (in a direction 806 from the source 708 to the detector array 716) at an outer region 802 of the half wedges 718$_1$ and 718$_2$ relative to an inner region 804 of the half wedges 718$_1$ and 718$_2$. Half wedges 718$_1$ and 718$_2$ more heavily filter the collimated beam 714 passing through the thicker outer regions 802 of the half wedges 718$_1$ and 718$_2$ relative to X-rays passing through the thinner inner region 804 of the half wedges 718$_1$ and 718$_2$. Due to its shape, the dynamic bowtie filter 718 varies the degree of the beam attenuation there between. The half wedges 718$_1$ and 718$_2$ may comprise a material(s) such as Teflon®, a product of Chemours, USA, aluminum oxide ($Al_2O_3$), and/or other material suitable for shaping a fluence profile of the beam 714 for CT scanning.

Figure 9:
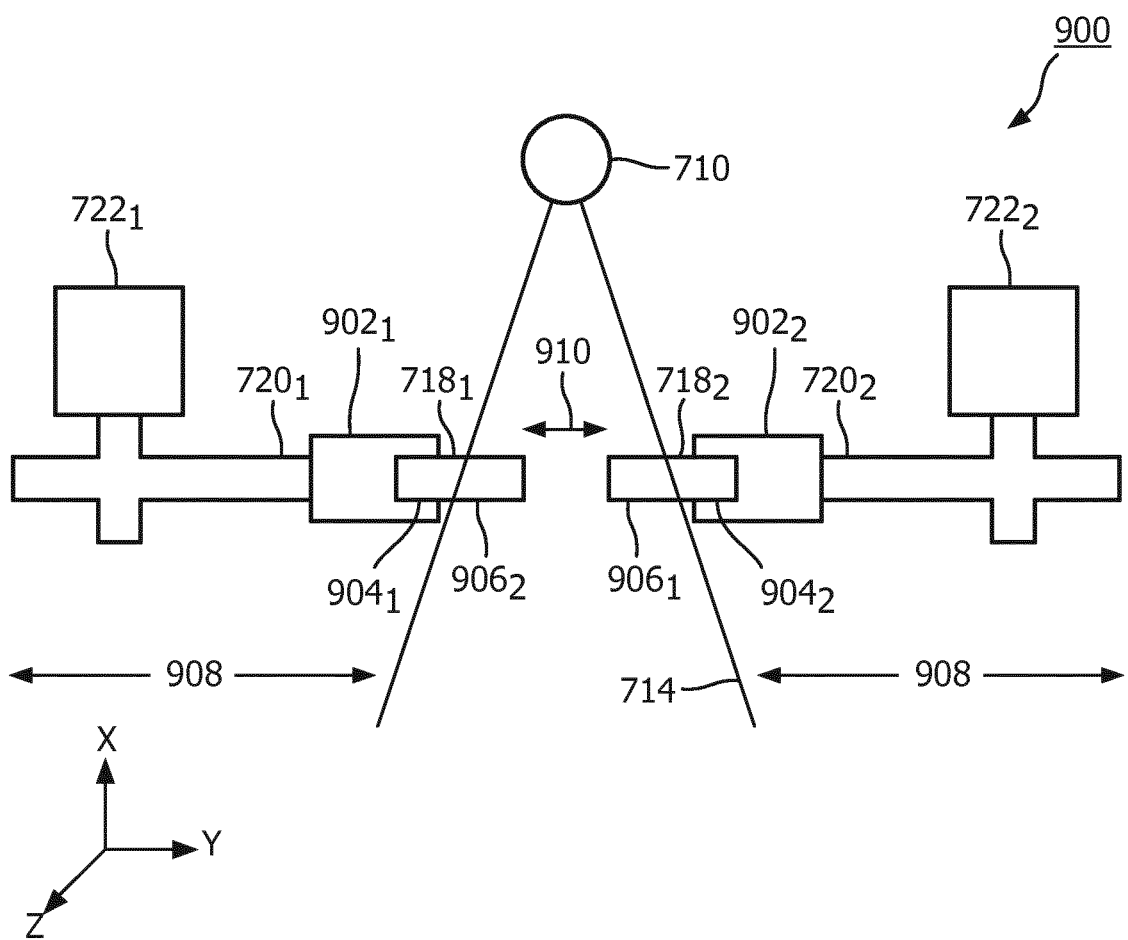
FIG. 9 diagrammatically illustrates a side view of an example of a drive system for the dynamic bowtie filter in accordance with an embodiment herein.
Figure 10:
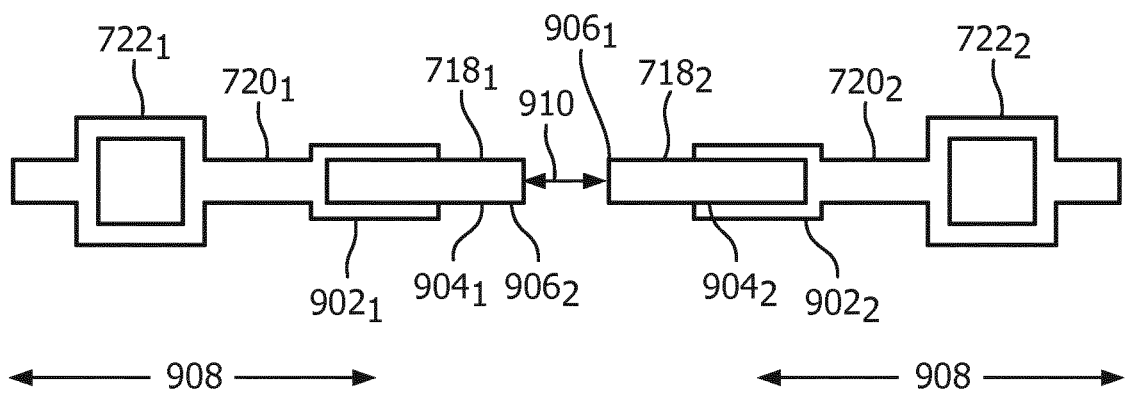
FIG. 10 diagrammatically illustrates a bottom view of the example of the drive system for the dynamic bowtie filter in accordance with an embodiment herein.

FIG. 9 diagrammatically illustrates a side view of an embodiment of a drive system 900 supporting the half wedges 718$_1$ and 718$_2$, and including half wedge holders 902$_1$ and 902$_2$, the movers 720$_1$ and 720$_2$, and the motors 722$_1$ and 722$_2$ from a view along a Z-axis direction. FIG. 10 diagrammatically illustrates a bottom view of the drive system 900. The half wedge holders 902$_1$ and 902$_2$ are coupled to outer regions 904$_1$ and 904$_2$ of the half wedges 718$_1$ and 718$_2$. The motors 722$_1$ and 722$_2$, in response to a command from the controller 730, adjust the position of the half wedge holders 902$_1$ and 902$_2$ so that the collimated beam 714 (collimator 712 not shown), emitted from the focal spot 710 of the source 708, transverses portions of inner region 906$_1$ and 906$_2$ of the half wedges 718$_1$ and 718$_2$, and not the half wedge holders 902$_1$ and 902$_2$.

In response to a command from the controller 724, the motors 722$_1$ and 722$_2$ may move (e.g., translate) the movers 720$_1$ and 720$_2$, and thereby the half wedges 718$_1$ and 718$_2$ in an X/Y-plane (e.g., a direction 908), which is transverse to the Z-axis direction or Z direction. In another embodiment, the half wedges 718$_1$ and 718$_2$ are moved in the X, Y, and/or Z direction at any distance. The movement may increase or decrease a distance 910 between the half wedges 718$_1$ and 718$_2$, before, during, and/or after an acquisition interval. Again, an acquisition interval, as used herein, refers to a period of time wherein the collimated beam 714 illuminates the detector array 716 and the detector array 716 detects the radiation over a predetermined angular increment of the rotating gantry 704 (also referred to as an integration period). Furthermore, the motors 722$_1$ and 722$_2$ may move only one of the half wedges 718$_1$ or 718$_2$, or move both, serially or in parallel, a same or different distance, towards or away from one another at the same time.

Figure 11:
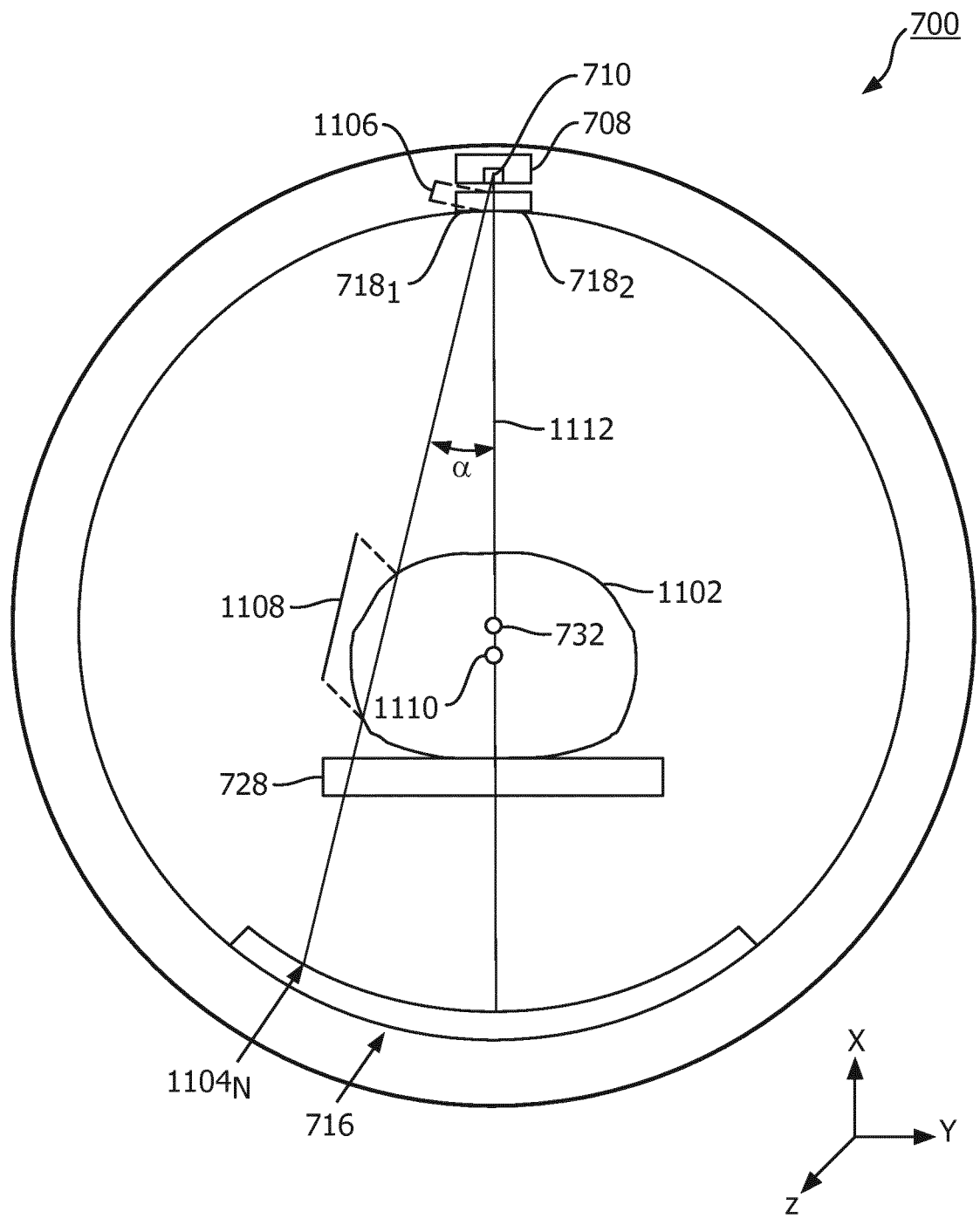
FIG. 11 diagrammatically illustrates an example of a subject or object in the imaging system in accordance with an embodiment herein.
Figure 12:
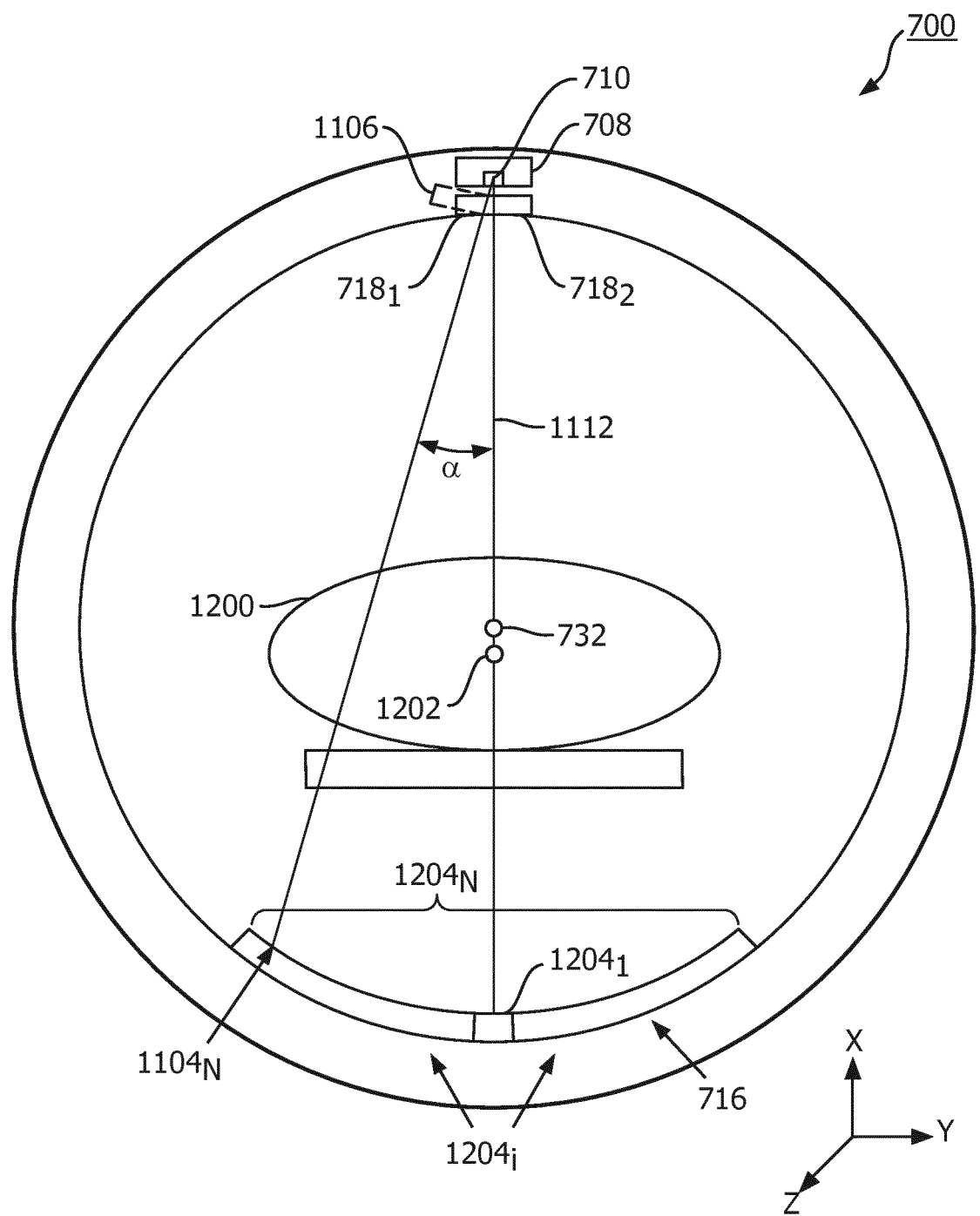
FIG. 12 diagrammatically illustrates an example of a mathematical body in the imaging system in accordance with an embodiment herein.

As briefly stated above, the dynamic bowtie filter 718 is configured to dynamically move one or both (individually and/or concurrently) of the wedges 718$_1$ and 718$_2$ to adjust the X-ray fluence profile. In one instance, the wedges 718$_1$ and/or 718$_2$ are dynamically translated (in or out on the X/Y-plane) until a fluence profile, across the detectors in the detector array 716, after traversing the dynamic bowtie filter 718 and the object or subject, satisfies a given acceptance criterion. FIGS. 11 and 12 describe a non-limiting approach for determining a fluence at the detectors in the detector array 716. FIG. 11 diagrammatically illustrates an example of a mis-centered object or subject 1102, and FIG. 12 diagrammatically illustrates using, conceptually, a water-equivalent mathematical ellipse 1200 to estimate the fluence at the detectors for the mis-centered object or subject in FIG. 11.

In FIG. 11, a center point 1110 of the mis-centered object or subject 1102 is below the iso-center 732. In general, an X-ray radiation fluence at a given detector 1104$_N$ of the detector array 716 is a function of an output of the radiation source 708 at an angle α from an x-ray 1112, an attenuation of the collimated beam 714 by the half wedges 718$_1$ and 718$_2$ (a half wedge path length 1106), an attenuation of the collimated beam 714 by the object or subject 1102 (an object or subject path length 1108), and scattered radiation from the object or subject being scanned incident on a detector 1104$_N$ of the detector array 716. Where a magnitude of the scattered radiation is negligible compared to a magnitude of the attenuated primary radiation (non-scatter radiation traversing from the source 708 to the detector array 716), a fluence at the given detector 1104$_N$ in the detector array can be determined as shown in EQUATION 1:

Fluence (at detector 1104$_N$)=(Output of the radiation source 708 at angle α) (attenuation of a half wedge 718$_1$ or 718$_2$ at the angle α) (attenuation of the object or subject 1102 at angle α).     EQUATION 1:

In FIG. 12, the console 730 conceptually replaces the object or subject 1102 with the water-equivalent mathematical ellipse 1200 centered at 1202, which is the center point 1110 of the mis-centered object or subject 1102.

For this, the imaging system 700 is operated to perform a survey scan (e.g., a scout, a surview, a pilot, etc. scan) to acquire a two or three-dimensional projection image(s) of the subject or object 1102. A contour of the subject or object is identified in the projection image(s) to estimate the boundary of the subject or object 1102. From the boundary, the console 730 creates the water-equivalent homogeneous ellipse 1200, wherein lengths of the major and minor axes of the ellipse are derived from the boundary of the object 1102. The console 730 determines the center point 1202 of the water-equivalent mathematical ellipse from projection image(s). The coordinates of the center point 1202 are determined for each axial slice and used to generate two half wedge position profiles, one for half wedge 718$_1$ and one for 718$_2$.

Figure 13:
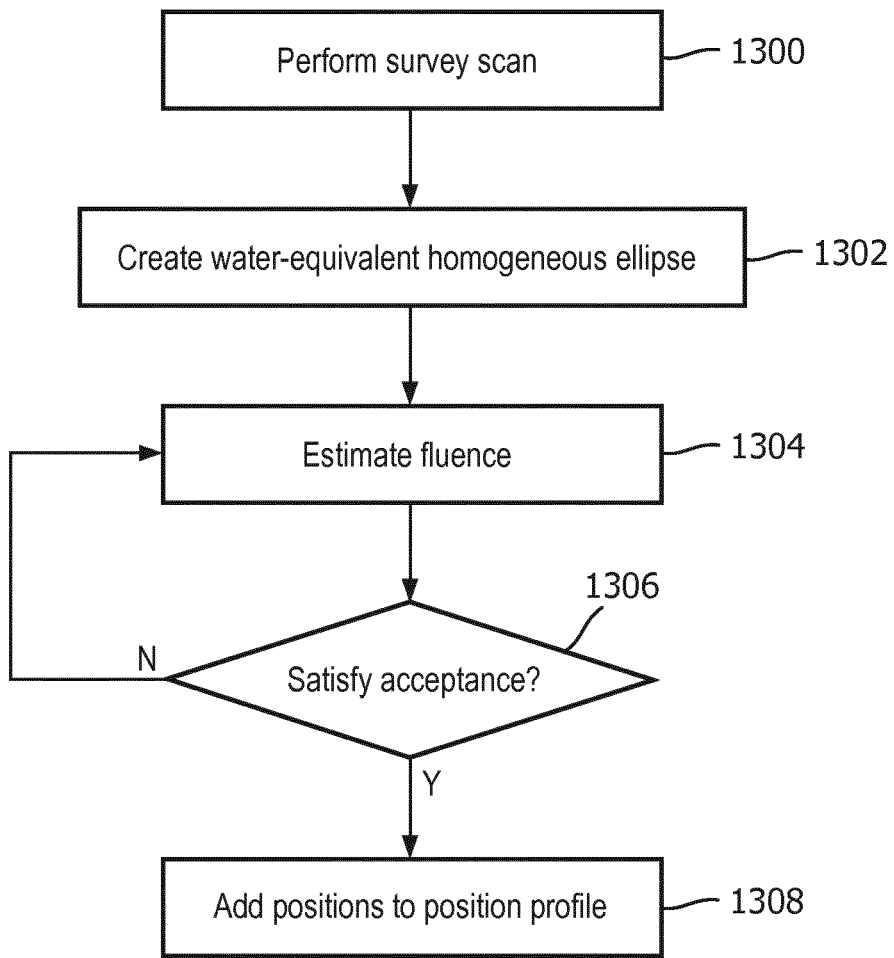
FIG. 13 diagrammatically illustrates an example of a method in accordance with an embodiment herein.

FIG. 13 illustrates a method which dynamically moves the wedges 718₁ and/or 718₂ to adjust the X-ray fluence profile based on the fluence estimate.

At 1300, a survey scan of a subject is performed, thereby producing a projection image.

At 1302, a water-equivalent homogeneous ellipse of the subject or object is created from the projection image, as described herein and/or otherwise.

At 1304, the console 730 mathematically estimates a fluence of a detector $1104_N$ with the first half wedge $718_1$ and the second half wedge $718_2$ at a current position.

At 1306, the console 730 determines if the estimated fluence satisfies a predetermined fluence acceptance criterion.

If so, then at 1308, the console 730 adds the position of the first half wedge $718_1$ and/or the second half wedge $718_2$ to a position profile.

If not, then steps 1302-1306 are repeated for a different position of the first half wedge $718_1$ and/or the second half wedge $718_2$.

Where there are more than one gantry rotation angle and/or more than one projection image the steps 1300-1308 are repeated for more than one gantry rotation angle and/or more than one projection image.

While the above example estimates the fluence at a single detector and determines if the estimated fluence for a single detector satisfies a predetermined fluence acceptance criterion, these steps may apply to all or less than all of the detectors.

A non-limiting example of the predetermined fluence acceptance criterion includes uniformity of signal across the detector. Examples of uniformity criteria include: no detector reading below a designated minimum and/or a % of the designated minimum, a least mean squared difference (from a designated value) for all/limited set of detector readings, etc. For sake of brevity, an example where the acceptance criteria include uniformity of the signal across the detectors is described below.

Figure 14:
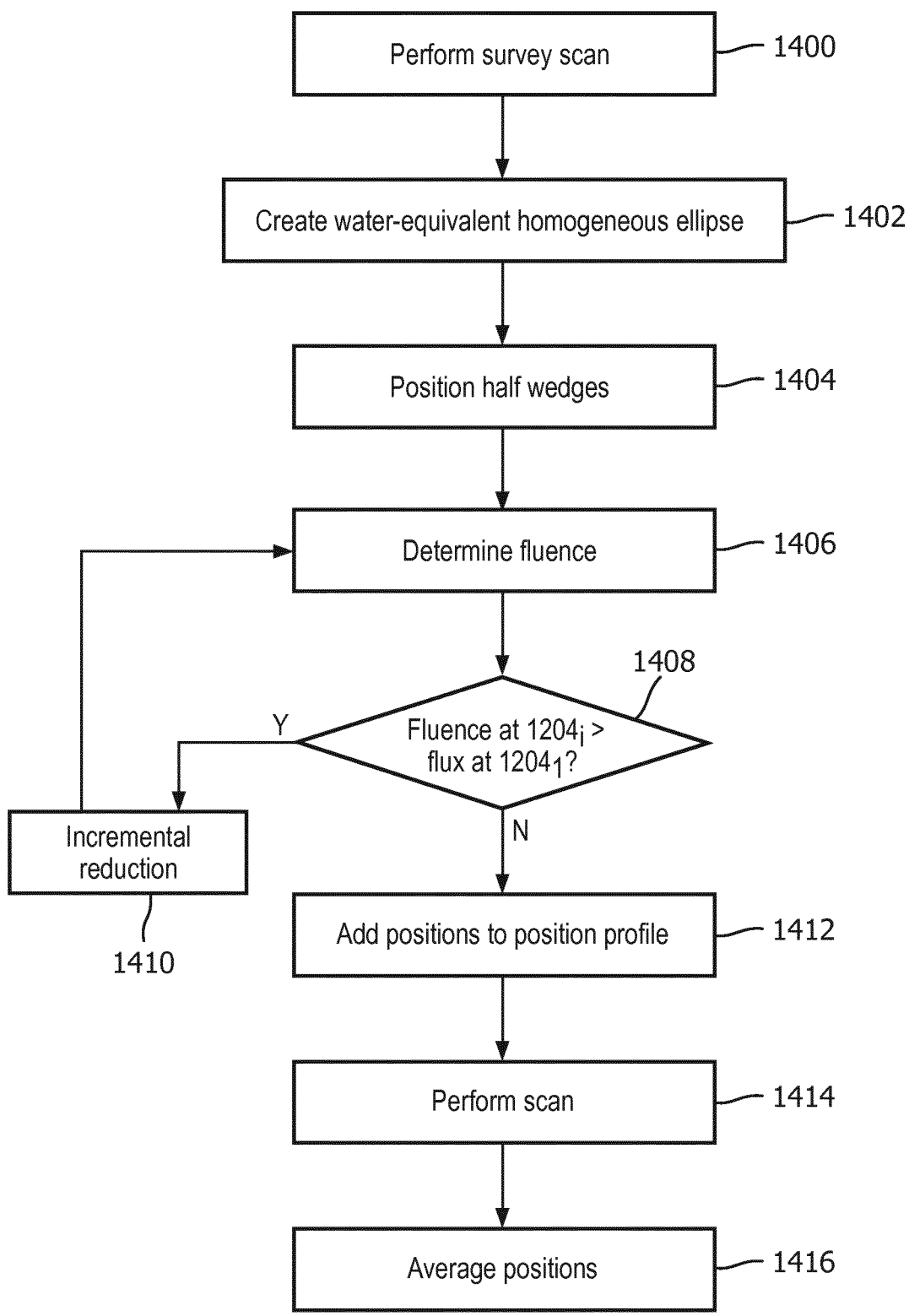
FIG. 14 shows a flowchart of a method in accordance with another embodiment of the present invention.

FIG. 14 illustrates a method which dynamically moves the wedges 718₁ and/or 718₂ to adjust the X-ray fluence profile based on the fluence estimate and a uniformity acceptance criterion of uniformity of the signal across all detectors.

At 1400, a survey scan of a subject or object is performed, thereby producing a projection image.

At 1402 a water-equivalent homogeneous ellipse of the subject or object is created for the projection image, as described herein and/or otherwise.

At 1404, the half wedges $718_1$ and $718_2$ are first positioned at a predetermined initial location $P_0$, e.g., the position with a maximum width between the two half wedges $718_1$ and $718_2$ or other position, as described herein and/or otherwise.

At 1406, a fluence through the water-equivalent mathematical ellipse at each detector in the detector array is calculated with the half wedges $718_1$ and $718_2$ at the location $P_0$, e.g., with EQUATION 1 and/or otherwise.

At 1408, the fluence for all the detectors $1204_i$, is compared to the fluence at detector $1204_1$.

If the fluence for all the detectors $1204_i$ is greater than the fluence at $1204_1$, then at 1410 the distance between half wedges $718_1$ and $718_2$ is reduced, as described herein and/or otherwise, thereby placing the half wedges $718_1$ and $718_2$ into position $P_N$, and acts 1406 and 1408 are repeated.

However, if the fluence for any of the detectors $1204_i$ is not greater (i.e. less) than the fluence at $1204_1$, then at 1412, the position $P_{N-1}$ (the previous position) for each half wedge $718_1$ and $718_2$ is added to a position profile.

At 1414 the imaging system 700 scans the subject or object 1102 wherein the drive system 900 moves the half wedges $718_1$ and $718_2$ based on the calculated half wedge positions during an acquisition interval.

At 1416, the controller 724 measures the half wedge $718_1$ and $718_2$ during an integration period, averages the measured half wedge positions for that integration period, and sends the averaged half wedge positions to the reconstructor 726.

In other words (and with reference to FIG. 12), with using the acceptance criterion of uniformity of the signal across all detectors $1204_N$ (and thereby minimizing over dose to the object or subject being scanned), the fluence for each angle is modulated (via moving the half wedge 718₁ and/or 718₂) so that the fluence at the detector $1204_1$ is a maximum fluence as compared to fluences at the other detectors $1204_i$ and the fluences at the other detectors $1204_i$ are modulated, via a half wedge setting, so that the fluences at the other detectors $1204_i$ are closer to the minimum fluence.

Where there are more than one gantry rotation angles and/or more than one projection images, then steps 1400-1412 are repeated for each gantry rotation angle/projection image. For the sake of brevity, the above example includes one gantry rotation angle and one projection image.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with, or as part of other hardware, but may also be distributed in other forms, such as via the Internet or other wired or wireless telecommunication systems. Any reference signs in the claims should not be construed as limiting the scope.

What is claimed is:

1. An imaging system, comprising:
   a radiation source configured to emit radiation that traverses an examination region;
   a radiation detector array having a plurality of detectors configured to detect the radiation traversing the examination region;
   a dynamic bowtie filter disposed between the radiation source and the examination region, wherein the dynamic bowtie filter comprises a first half wedge and a separate and distinct second half wedge with a material free space therebetween;
a first motor in mechanical communication with the first half wedge, wherein the first motor is configured to move the first half wedge;
a second motor in mechanical communication with the second half wedge, wherein the second motor is configured to move the second half wedge; and
controller circuitry configured to independently control the first and second motors to move the first and second half wedges to increase or decrease a distance therebetween during an acquisition interval,
wherein the controller circuitry is further configured to, prior to the moving of the first half wedge and the second half wedge:
perform a survey scan of the subject of object to produce a projection image of the subject of object;
identify a contour and a center point of the subject or object from the projection image;
create a wafer-equivalent homogenous ellipse for the subject of object using the center point; and
determine the predetermined wedge position profile based on the water-equivalent homogeneous ellipse.

2. The system of claim 1, wherein the first half wedge and the second half wedge have a same size, shape, and density.

3. The system of claim 1, wherein the controller circuitry is configured to move the first half wedge and second half wedge in a same direction at a point in time.

4. The system of claim 1, wherein the controller circuitry is configured to move the first half wedge and second half wedge in opposite directions at a point in time.

5. The system of claim 1, wherein the first and second motors are linear motors.

6. The system of claim 5, wherein the controller circuitry is further configured to determine a geometric center of an object or subject by creating a mathematical body from a survey scan of the object or subject.

7. The system of claim 1, wherein the controller circuitry is configured to move at least one of the first half wedge and the second half wedge from a first location to a different location, which reduces an x-ray fluence at the radiation detector array.

8. The system of claim 1, further comprising:
a first mover and a second mover, wherein the first mover is coupled to a first half wedge holder and the first motor, and the second mover is coupled to the second half wedge holder and the second motor, and the first half wedge holder is coupled to the first half wedge, and the second half wedge holder is coupled to the second half wedge.

9. The imaging system according to claim 1, wherein the first half wedge and the second half wedge do not overlap in a direction from the radiation source to the radiation detector array.

10. An imaging method, comprising:
emitting, from a radiation source, radiation that traverses an examination region;
detecting, by a radiation detector array, the radiation traversing the examination region;
providing a dynamic bowtie filter between the radiation source and the examination region;
attenuating rays of the emitted radiation during a scan of a subject or object with the dynamic bowtie filter, wherein the dynamic bowtie filter comprises a first half wedge and a second half wedge with a material free space therebetween; and
independently moving, with a controller, the first half wedge and the second half wedge to increase or decrease a distance therebetween during a scan based on a predetermined wedge position profile,
wherein the method further comprises, prior to the independently moving of the first half wedge and the second half wedge:
performing a survey scan of the subject or object to produce a projection image of the subject or object;
identifying a contour and a center point of the subject or object from the projection image;
creating a water-equivalent homogeneous ellipse for the subject or object using the center point; and
determine the predetermined wedge position profile based on the water-equivalent homogeneous ellipse.

11. The method of claim 10, further comprising:
determining a position of the first half wedge or the second half wedge at which a fluence at a detector satisfies a predetermined fluence acceptance criterion.

12. The method of claim 11, further comprising:
creating the predetermined wedge position profile with positions of the first half wedge and the second half wedge at which fluences at the detectors satisfy the predetermined fluence acceptance criterion.

13. The method according to claim 10, wherein the first half wedge and the second half wedge do not overlap in a direction from the radiation source to the radiation detector array.

\* \* \* \* \*